United States Patent
Chen et al.

(10) Patent No.: US 10,420,811 B2
(45) Date of Patent: Sep. 24, 2019

(54) CULTIVATION OF SELENIUM-RICH CYCLOCARYA PALIURUS PLANT, EXTRACTION AND USE OF ACTIVE INGREDIENTS THEREOF

(71) Applicant: INFINITUS (CHINA) COMPANY LTD., Jiang Men (CN)

(72) Inventors: Weihong Chen, Jiang Men (CN); Fangli Ma, Jiang Men (CN); Wei Liu, Jiang Men (CN); Meng L V, Jiang Men (CN); Chung Wah Ma, Jiang Men (CN)

(73) Assignee: INFINITUS (CHINA) COMPANY LTD., Jiang Men (CN)

( * ) Notice: Subject to any disclaimer, the term of this patent is extended or adjusted under 35 U.S.C. 154(b) by 0 days.

(21) Appl. No.: 15/367,372

(22) Filed: Dec. 2, 2016

(65) Prior Publication Data
US 2017/0173098 A1 Jun. 22, 2017

(30) Foreign Application Priority Data

Dec. 16, 2015 (CN) .......................... 2015 1 0944402

(51) Int. Cl.
| | | |
|---|---|---|
| *A01N 25/02* | (2006.01) | |
| *A01N 59/16* | (2006.01) | |
| *C05G 3/00* | (2006.01) | |
| *A61K 36/52* | (2006.01) | |
| *A23L 33/105* | (2016.01) | |
| *A01N 25/30* | (2006.01) | |
| *A01N 37/02* | (2006.01) | |
| *A01N 37/18* | (2006.01) | |
| *A01N 43/22* | (2006.01) | |
| *A61K 33/00* | (2006.01) | |
| *C05D 9/02* | (2006.01) | |
| *C05G 3/06* | (2006.01) | |
| *C05G 3/02* | (2006.01) | |
| *C05D 3/02* | (2006.01) | |

(52) U.S. Cl.
CPC .............. *A61K 36/52* (2013.01); *A01N 25/02* (2013.01); *A01N 25/30* (2013.01); *A01N 37/02* (2013.01); *A01N 37/18* (2013.01); *A01N 43/22* (2013.01); *A01N 59/16* (2013.01); *A23L 33/105* (2016.08); *A61K 33/00* (2013.01); *C05D 9/02* (2013.01); *C05G 3/00* (2013.01); *C05G 3/02* (2013.01); *C05G 3/06* (2013.01); *A23V 2002/00* (2013.01); *A61K 2236/33* (2013.01); *A61K 2236/51* (2013.01); *A61K 2236/53* (2013.01)

(58) Field of Classification Search
None
See application file for complete search history.

(56) References Cited

U.S. PATENT DOCUMENTS

2009/0078014 A1* 3/2009 Yamashita ............... C05D 9/02
71/11

FOREIGN PATENT DOCUMENTS

| CN | 103664286 | * | 3/2014 |
| CN | 104026311 | * | 9/2014 |

OTHER PUBLICATIONS

English Machine Translation of CN 104026311 [online].Espacenet Oct. 24, 2017 [retrieved on Oct. 24, 2017]. Retrieved from the internet: <www.espacenet.com>.*
English Machine Translation of CN 103664286 [online].Espacenet Oct. 24, 2017 [retrieved on Oct. 24, 2017]. Retrieved from the internet: <www.espacenet.com>.*

* cited by examiner

*Primary Examiner* — Katherine Peebles
(74) *Attorney, Agent, or Firm* — Parker Highlander PLLC

(57) ABSTRACT

The present invention relates to cultivation of a selenium-rich *Cyclocarya paliurus* plant, extraction and use of active ingredients thereof, for overcoming disadvantages of high residue, poor absorption, and less environmental friendliness of fertilizers used in cultivation of a selenium-rich plant in the prior art, and overcoming disadvantages of low absorption rate and high adverse reaction rate in current extraction method and application of active ingredients in a selenium-rich plant. The present invention provides a method of cultivating a selenium-rich *Cyclocarya paliurus* plant, comprising use of a selenium-rich organic fertilizer during the cultivation, wherein the selenium-rich organic fertilizer comprises a selenium-rich yeast, a humic acid, an amino acid, a plant growth regulator and a foliar penetration enhancer. The present invention also provides a method for extracting active ingredients of the selenium-rich *Cyclocarya paliurus* plant obtained by the above method, comprising pretreatment, extraction, concentration and alcohol precipitation to obtain a crude extract.

2 Claims, No Drawings

CULTIVATION OF SELENIUM-RICH *CYCLOCARYA PALIURUS* PLANT, EXTRACTION AND USE OF ACTIVE INGREDIENTS THEREOF

CROSS REFERENCE OF RELATED APPLICATION

This application claims the benefit of priority to Chinese Patent Application No. 201510944402.1 filed on Dec. 16, 2015. The entire content of the above-referenced disclosure is specifically incorporated herein by reference.

FIELD

The present invention relates to the field of deep processing of natural plants, and particularly to cultivation of a selenium-rich *Cyclocarya paliurus* plant, extraction and use of active ingredients thereof.

BACKGROUND

Diabetes is a metabolic disease accompanied by increased blood glucose. It mainly comprises two types, i.e. Type I and Type II, with the latter being in the majority and accounting for 90% of patients with diabetes. Type II diabetes is mainly characterized by insulin resistance, in which uptake of glucose in liver, skeletal muscle and tissues such as adipose is decreased, leading to an increase of blood glucose level to result in high blood glucose. *Cyclocarya paliurus* is a deciduous tree of Juglandaceae family, and also named as Qing Qian plum or Jin Qian willow. It mainly grows in the southern mountain area in China at an altitude of 800 to 2000 meters which is dump and foggy. It is a monotypic plant unique to China. *Cyclocarya paliurus* comprises various active ingredients such as polysaccharides, flavonoids, triterpenoid saponins, and alkaloids. There have been researches showing significant effects such as reduction of blood glucose and blood lipid of the active ingredients. It has been found through researches that the extract of *Cyclocarya paliurus* plant can significantly enhance the tolerance ability of mice with diabetes induced by alloxan to glucose, has a strong inhibitory effect on the activity of α-glucosidase, can facilitate restoration of the structure and function of diseased islet, enhance the glucose tolerance of mice, and lower the fasting blood glucose level. Meanwhile, the extract of *Cyclocarya paliurus* plant also has obvious effects of improving blood lipid metabolism and enhancing antioxidant ability of the body. It can also inhibit the expression of FAS gene and protein in mice with hyperlipidemia. Therefore, there is a good prospect in developing the active ingredients of *Cyclocarya paliurus* plant as health food and medicament that lowers blood glucose level and blood lipid level, etc.

In recent years, the development of natural selenium-rich health products has attracted people's attention. Selenium is an important nutrient element essential for human body. It has physiological functions such as promotion of human body immunity, anti-oxidation, anti-aging, anti-cancer, and antagonization of heavy metal toxicity. Researches have shown that the occurrence and development of more than 40 types of diseases including Keshan disease, Kashin-Beck disease and diabetes are closely associated with selenium deficiency in human body. Currently, the standard of selenium daily intake amount by human body recommended by Chinese Nutrition Society is 50 to 250 µg, while the daily intake amount of selenium by adults is only 20 to 30 µg in China at present, which indicates a serious insufficiency of selenium intake. Problems such as low absorption rate in human body and high toxic side effects are present in inorganic selenium. Organic selenium is consistent with the natural form of selenium existing in human body and is easy to stay and accumulate in body, whereby the bioavailability is significantly increased with low toxic side effects. Therefore, it is necessary to develop a natural selenium-rich health product.

Currently, it is one of the simplest and most effective ways to obtain selenium-rich products by adding artificial selenium-rich fertilizers to render plants selenium-rich. However, selenium-rich fertilizers currently used in great amount are mainly produced from selenium ore powder or sodium selenite. Selenium ores always comprise many kinds of other heavy metals, and may make heavy metal concentration in soil and plants go beyond limits very easily. Sodium selenite is hard to be absorbed and transformed by plants. Large amount of unabsorbed sodium selenite will cause pollution to soil, water body and the surrounding environment. Furthermore, sodium selenite is toxic per se, and thus the residual sodium selenite on the surface of plants could cause damage to the health of human to some extent.

In view of the above, fertilizers used in cultivation of a selenium-rich plant in the prior art have disadvantages of high residue, poor absorption, and less environmental friendliness. Meanwhile, the current extraction and application of active ingredients in a selenium-rich plant have disadvantages of low absorption rate and high adverse reaction rate.

Accordingly, there is an urgent need for the skilled in the art to develop a selenium-rich organic fertilizer with high absorption rate, low residue and no harm to environment, and meanwhile to develop a method for extracting a selenium-rich plant with high absorption rate of active ingredients and less adverse reaction and the corresponding application thereof.

SUMMARY

An example of the present invention provides a method for cultivation of a selenium-rich *Cyclocarya paliurus* plant as well as extraction and application of active ingredients thereof for overcoming disadvantages of high residue, poor absorption, and less environmental friendliness of fertilizers used in cultivation of a selenium-rich plant in the prior art, and meanwhile overcoming disadvantages of low absorption rate and high adverse reaction rate in current extraction method and application of active ingredients in a selenium-rich plant.

A method of cultivating a selenium-rich *Cyclocarya paliurus* plant provided by an example of the present invention comprises use of a selenium-rich organic fertilizer during the cultivation of the selenium-rich *Cyclocarya paliurus* plant; wherein the selenium-rich organic fertilizer comprises a selenium-rich yeast, a humic acid, an amino acid, a plant growth regulator and a foliar penetration enhancer.

Preferably, calculated in parts by weight, the selenium-rich organic fertilizer comprises: 1.0 to 10.0 parts of the selenium-rich yeast, 10.0 to 70.0 parts of the humic acid, 1.0 to 50.0 parts of the amino acid, 0.5 to 10.0 parts of the plant growth regulator and 0.5 to 20.0 parts of the foliar penetration enhancer.

The present invention provides a method of preparing an extract of the selenium-rich *Cyclocarya paliurus* plant, comprising extracting an extract of the selenium-rich *Cyclo-*

*carya paliurus* plant from leaves of *Cyclocarya paliurus* plant, with a selenium-rich organic fertilizer used during the cultivation of the *Cyclocarya paliurus* plant; the selenium-rich organic fertilizer comprising a selenium-rich yeast, a humic acid, an amino acid, a plant growth regulator and a foliar penetration enhancer.

Wherein, calculated in parts by weight, the selenium-rich organic fertilizer comprises 1.0 to 10.0 parts of the selenium-rich yeast, 10.0 to 70.0 parts of the humic acid, 1.0 to 50.0 parts of the amino acid, 0.5 to 10.0 parts of the plant growth regulator and 0.5 to 20.0 parts of the foliar penetration enhancer.

Preferably, by mass percentage, the basic composition of the selenium-rich organic fertilizer is: 1.0 to 10.0% of the selenium-rich yeast, 10.0 to 70.0% of the humic acid, 1.0 to 50.0% of the amino acid, 0.5 to 10.0% of the plant growth regulator, 0.5 to 20.0% of the foliar penetration enhancer, respectively, with the total percentage of the above components of 100%.

Preferably, by mass percentage, the basic composition of the active selenium-rich organic fertilizer is: 3.0 to 6.0% of the selenium-rich yeast, 20.0 to 55.0% of the humic acid, 1.0 to 40.0% of the amino acid, 1.0 to 5.0% of the plant growth regulator, 2.0 to 15.0% of the foliar penetration enhancer, respectively, with the total percentage of the above components of 100%.

Preferably, the amino acid is one or more selected from the group consisting of cysteine, methionine, alanine, isoleucine, aspartate, glutamate, lysine, glycine and serine; the plant growth regulator is one or a mixture of more than one selected from the group consisting of titanyl sulfate, titanium diacetamide tetraacetate, titanium ethylenediamine-di-o-phenyl acetate, zinc sulfate, zinc acetamide tetraacetate, zinc ethylenediamine-di-o-phenyl acetate, magnesium chloride, magnesium acetamide tetraacetate, magnesium ethylenediamine-di-o-phenyl acetate, propionyl brassinolide, sodium nitrophenolate, 1-methyl propylene and methyl jasmonate; the foliar penetration enhancer is one or more selected from the group consisting of sodium lauryl sulfate, calcium chloride, titanyl sulfate, ferrous sulfate, tributyl phosphate, diethyl sebacate and diethyl octanedioate.

Preferably, the cultivation method further comprises mixing the selenium-rich organic fertilizer with a commercially available conventional compound fertilizer, and the mass ratio of the selenium-rich organic fertilizer to the commercially available conventional compound fertilizer is 1:(100~2000).

Preferably, the cultivation method further comprises dissolving the selenium-rich organic fertilizer in water, and the mass ratio of the selenium-rich organic fertilizer to water is 1:(100~1000).

Preferably, the cultivation method comprises mixing the selenium-rich organic fertilizer with a general compound fertilizer by a mass ratio of 1:100~1:2000 and then performing soil fertilization. During soil fertilization, the ratio of fertilizing amount of the mixed fertilizer to the height of the *Cyclocarya paliurus* plant is 1 kg:(1-2) m.

Preferably, the cultivation method comprises dissolving the selenium-rich organic fertilizer in water by a mass ratio of 1:100 to 1:1000 to formulate an aqueous solution, and then performing foliar spray.

An example of the present invention further provides a method for extracting active ingredients of the selenium-rich *Cyclocarya paliurus* plant obtained by any one of the cultivation methods as described above, comprising: pretreatment, extraction, concentration and alcohol precipitation, to obtain a crude extract; wherein the pretreatment comprises purification, washing and smashing to obtain a first product; the extraction comprises mixing the first product with an extracting liquid and extracting by heating under reflux to obtain a second product; the concentration comprises subjecting the second product to concentration under reduced pressure or concentration by ultrafiltration membrane to obtain a third product; the alcohol precipitation comprises adding ethanol to the third product and collecting precipitate by filtration, wherein the precipitate is the crude extract.

Preferably, the particle size of the first product is 10 to 100 meshes; the extracting liquid is one or more selected from water, ethanol, NaOH solution, HCl solution, NaCl solution, Tris-HCl solution and PBS solution; the heating temperature is 40 to 100° C.; the time period for extraction is 0.5 to 5 h; the extraction is carried out for 1 to 10 times; the volume ratio of the third product to the second product is 1:(5~20); the volume ratio of ethanol to the third product is (1~9):1.

Preferably, the extraction method further comprises refining and drying to obtain the crude extract; the refining and the drying are sequentially performed after the alcohol precipitation.

Preferably, the refining is carried out by redissolving the crude extract followed by mixing with a flocculant, heating under stirring, and collecting the filtrate after filtration; the drying is performed by one or more selected from freeze drying, hot air drying under normal pressure, vacuum drying, spray drying, microwave drying and infrared drying; the mass ratio of the flocculant to the crude extract is (0.5~5):10; the flocculant is one or more selected from chitosan, carboxymethyl chitosan, quaternary ammonium chitosan, gelatin and ZTCl+1 clarificant (the ZTCl+1 clarificant used herein is a mixture of commercially available chitosan and calcium carbonate); the heating under stirring is carried out at a temperature of 40 to 60° C. for 0.05 to 2 h.

An example of the present invention further provides use of a dosage form prepared from the product obtained by any one of the extraction methods as described above in health food and/or medicament. The dosage form includes, but is not limited to, tablets, capsules, granules, drop pills and oral liquid.

An example of the present invention further provides use of a dosage form prepared from the product obtained by any one of the extraction methods as described above in hypolipidemic and hypoglycemic health food or medicament. The dosage form includes, but is not limited to, tablets, capsules, granules, drop pills and oral liquid. In view of the above, cultivation of a selenium-rich *Cyclocarya paliurus* plant, extraction and use of active ingredients of the selenium-rich *Cyclocarya paliurus* plant as provided by an example of the present invention overcome the disadvantages of high residue, poor absorption, and less environmental friendliness of fertilizers used in cultivation of a selenium-rich plant in the prior art, and meanwhile overcome the disadvantages of low absorption rate and high adverse reaction rate in current extraction method and application of active ingredients in a selenium-rich plant.

DETAILED DESCRIPTION

Technical solutions in examples of the present invention will be clearly and completely described below. It is apparent that the described examples merely constitute a part rather than all of the examples of the present invention. All of the other examples obtained by an ordinary skilled in the art without any creative work based on the examples of the present invention fall within the protection scope of the present invention.

It is a challenge for those skilled in the art to achieve selenium enrichment in plants. An example of the present invention obtained a novel active selenium-rich organic fertilizer with a unique formulation through experimentation and screening, which can effectively achieve selenium-enrichment in *Cyclocarya paliurus* plant upon application on *Cyclocarya paliurus* plant. The selenium content in leaves of the selenium-rich *Cyclocarya paliurus* plant can be up to 20.0 mg/kg, and that in the extract of the selenium-rich *Cyclocarya paliurus* plant can be up to 10.0 mg/kg. Meanwhile, the active selenium-rich organic fertilizer provided in the present invention is an organic fertilizer, which avoids the problems of low transformation rate of selenium, high toxic side effects, and environmental pollution in inorganic selenium fertilizers.

Meanwhile, the technical solutions of the present invention successfully achieve an efficient transformation of selenium in plant body. The obtained extract of selenium-rich *Cyclocarya paliurus* plant not only contains effective ingredients such as *Cyclocarya paliurus* polysaccharide, but also is rich in the trace element selenium. It has been illustrated via animal experiments that such extract of selenium-rich *Cyclocarya paliurus* plant has significant efficacies of simultaneously lowering blood glucose, lowering blood lipid, and improving body immunity, etc.

In the technical solutions provided in the present invention, the employed fertilization technology for selenium-rich *Cyclocarya paliurus* plant and extraction technology for the extract of selenium-rich *Cyclocarya paliurus* plant are simple and practicable, and facilitate large-scale production.

In order to illustrate the present invention in more detail, the cultivation of the selenium-rich *Cyclocarya paliurus* plant, extraction and use of the active ingredients of the selenium-rich *Cyclocarya paliurus* plant as provided in the present invention are specifically described in conjunction with examples as follows.

Selenium contents in leaves of the selenium-rich *Cyclocarya paliurus* plant and extract of the selenium-rich *Cyclocarya paliurus* plant obtained by the present technical solution are detected with Atomic Fluorescence Spectrometry according to the national standard testing specification GB5009.93-2010. The content of *Cyclocarya paliurus* polysaccharide is detected by anthrone-sulfuric acid method according to "Chinese Pharmacopoeia" section 1, edition 2015.

Example 1

The composition of the active selenium-rich organic fertilizer was (by mass ratio): 6% of selenium-rich yeast, 47% of humic acid, 24% of cysteine, 10% of methionine, 5% of titanium ethylenediamine-di-o-phenyl acetate and 8% of ferrous sulfate, which were mixed to obtain the selenium-rich organic fertilizer 1. The selenium-rich organic fertilizer 1 was mixed with a commercial-available ordinary compound fertilizer with a ratio of 1:800 and then applied to fertilize an 8 m high *Cyclocarya paliurus* plant via soil fertilization with a total amount of 4 kg. The fertilization was carried out once on November of winter. Leaves were collected in April of the next year. The content of selenium in leaves of *Cyclocarya paliurus* plant was measured to be 2.6 mg/kg.

The collected leaves of *Cyclocarya paliurus* plant as described above were purified, washed, and then smashed into 40 meshes, to obtain a first product 1. The first product 1 was weighed and added with water by a mass ratio of 1:15 (leaves to water). The extraction was carried out twice under reflux for 3 h at a temperature of 100° C. After filtration, the filtrates were combined to obtain a second product 1. The second product 1 was concentrated by ultrafiltration membrane to obtain a third product 1. The volume ratio of the third product 1 to the second product 1 was 1:10. Ethanol was added into the third product 1 at a volume ratio of 4:1 (ethanol to the third product 1). After filtration, the obtained precipitate was the crude extract 1. The crude extract 1 was dissolved in water. Chitosan was added by a mass ratio of 2:10 (chitosan to the crude extract 1). The mixture was stirred for 0.5 h at a temperature of 50° C. and filtered. The filtrate was subjected to spray drying to obtain a product 1. The yield of the extract of selenium-rich *Cyclocarya paliurus* plant was 4.9%, which comprised 1.8 mg/kg of selenium and 22.3% of *Cyclocarya paliurus* polysaccharide.

Example 2

The composition of the active selenium-rich organic fertilizer was (by mass ratio): 1% of selenium-rich yeast, 49.5% of humic acid, 14% of cysteine, 15% of methionine, 0.5% of titanium ethylenediamine-di-o-phenyl acetate and 20% of sodium lauryl sulfate, which were mixed to obtain the selenium-rich organic fertilizer 2. The selenium-rich organic fertilizer 2 was mixed with a commercial-available ordinary compound fertilizer with a ratio of 1:100 and then applied to fertilize a 1 m high *Cyclocarya paliurus* plant via soil fertilization with a total amount of 1 kg. The fertilization was carried out once on December of winter. Leaves were collected in June of the next year. The content of selenium in leaves of *Cyclocarya paliurus* plant was measured to be 0.54 mg/kg.

The collected leaves of *Cyclocarya paliurus* plant as described above were purified, washed, and then smashed into 60 meshes, to obtain a first product 2. The first product 2 was weighed and added with 0.1 mol/L NaOH solution by a mass ratio of 1:4 (leaves to NaOH solution). The extraction was carried out once under reflux for 5 h at a temperature of 40° C. After filtration, the filtrates were combined to obtain a second product 2. The second product 2 was concentrated under reduced pressure to obtain a third product 2. The volume ratio of the third product 2 to the second product 2 was 1:10. Ethanol was added into the third product 2 at a volume ratio of 4:1 (ethanol to the third product 2). After filtration, the obtained precipitate was the crude extract 2. The crude extract 2 was dissolved in water. ZTCl+1 (a mixture of commercial available chitosan and calcium carbonate) was added by a mass ratio of 1.5:10 (ZTCl+1 to the crude extract 2). The mixture was stirred for 0.05 h at a temperature of 50° C. and filtered. The filtrate was subjected to spray drying to obtain a product 2. The yield of the extract of selenium-rich *Cyclocarya paliurus* plant was 1.2%, which comprised 0.48 mg/kg of selenium and 18.7% of *Cyclocarya paliurus* polysaccharide.

Example 3

The composition of the active selenium-rich organic fertilizer was (by mass ratio): 5% of selenium-rich yeast, 53.5% of humic acid, 20% of glycine, 15% of lysine, 2% of alanine, 3% of isoleucine, 1% of magnesium acetamide tetraacetate and 0.5% of ferrous sulfate, which were mixed to obtain the selenium-rich organic fertilizer 3. The selenium-rich organic fertilizer 3 was mixed with a commercial-available ordinary compound fertilizer with a ratio of 1:600 and then applied to fertilize a 5 m high *Cyclocarya paliurus* plant via soil fertilization with a total amount of 3 kg. The fertilization was carried out once on December of winter. Leaves were collected in August of the next year. The content of selenium in leaves of *Cyclocarya paliurus* plant was measured to be 1.33 mg/kg.

The collected leaves of *Cyclocarya paliurus* plant as described above were purified, washed, and then smashed into 40 meshes, to obtain a first product 3. The first product 3 was weighed and added with 0.5 mol/L sodium chloride solution by a mass ratio of 1:15 (leaves to sodium chloride solution). The extraction was carried out twice under reflux for 3 h at a temperature of 100° C. After filtration, the filtrates were combined to obtain a second product 3. The second product 3 was concentrated under reduced pressure to obtain a third product 3. The volume ratio of the third product 3 to the second product 3 was 1:5. Ethanol was added into the third product 3 at a volume ratio of 3:1 (ethanol to the third product 3). After filtration, the obtained precipitate was the crude extract 3. The crude extract 3 was dissolved in water. Chitosan was added by a mass ratio of 1:10 (chitosan to the crude extract 3). The mixture was stirred for 2 h at a temperature of 40° C. and filtered. The filtrate was subjected to freeze drying to obtain a product 3. The yield of the extract of selenium-rich *Cyclocarya paliurus* plant was 4.6%, which comprised 0.92 mg/kg of selenium and 18.2% of *Cyclocarya paliurus* polysaccharide.

Example 4

The composition of the active selenium-rich organic fertilizer was (by mass ratio): 10% of selenium-rich yeast, 70% of humic acid, 1% of cysteine, 10% of propionyl brassinolide and 9% of calcium chloride, which were mixed to obtain the selenium-rich organic fertilizer 4. The selenium-rich organic fertilizer 4 was mixed with a commercial-available ordinary compound fertilizer with a ratio of 1:400 and then applied to fertilize a 4 m high *Cyclocarya paliurus* plant via soil fertilization with a total amount of 2 kg. The fertilization was carried out once on January of winter. Leaves were collected in May of the next year. The content of selenium in leaves of *Cyclocarya paliurus* plant was measured to be 1.73 mg/kg.

The collected leaves of *Cyclocarya paliurus* plant as described above were purified, washed, and then smashed into 100 meshes, to obtain a first product 4. The first product 4 was weighed and added with water by a mass ratio of 1:15 (leaves to water). The extraction was carried out for 10 times under reflux for 0.5 h at a temperature of 90° C. After filtration, the filtrates were combined to obtain a second product 4. The second product 4 was concentrated by ultrafiltration membrane to obtain a third product 4. The volume ratio of the third product 4 to the second product 4 was 1:10. Ethanol was added into the third product 4 at a volume ratio of 1:1 (ethanol to the third product 4). After filtration, the obtained precipitate was the crude extract 4. The crude extract 4 was dissolved in water. Carboxymethyl chitosan was added by a mass ratio of 4:10 (carboxymethyl chitosan to the crude extract 4). The mixture was stirred for 0.5 h at a temperature of 50° C. and filtered. The filtrate was subjected to freeze drying to obtain a product 4. The yield of the extract of selenium-rich *Cyclocarya paliurus* plant was 6.2%, which comprised 1.36 mg/kg of selenium and 22.5% of *Cyclocarya paliurus* polysaccharide.

Example 5

The composition of the active selenium-rich organic fertilizer was (by mass ratio): 4% of selenium-rich yeast, 62% of humic acid, 12% of cysteine, 8% of methionine, 2% of zinc ethylenediamine-di-o-phenyl acetate and 12% of tributyl phosphate, which were mixed to obtain the selenium-rich organic fertilizer 5. The selenium-rich organic fertilizer 5 was mixed with a commercial-available ordinary compound fertilizer with a ratio of 1:2000 and then applied to fertilize a 6 m high *Cyclocarya paliurus* plant via soil fertilization with a total amount of 3 kg. The fertilization was carried out once on November of winter. Leaves were collected in April of the next year. The content of selenium in leaves of *Cyclocarya paliurus* plant was measured to be 0.75 mg/kg.

The collected leaves of *Cyclocarya paliurus* plant as described above were purified, washed, and then smashed into 10 meshes, to obtain a first product 5. The first product 5 was weighed and added with 0.1 mol/L HCl solution by a mass ratio of 1:15 (leaves to HCl solution). The extraction was carried out for 3 times under reflux for 2 h at a temperature of 100° C. After filtration, the filtrates were combined to obtain a second product 5. The second product 5 was concentrated under reduced pressure to obtain a third product 5. The volume ratio of the third product 5 to the second product 5 was 1:10. Ethanol was added into the third product 5 at a volume ratio of 1:1 (ethanol to the third product 5). After filtration, the obtained precipitate was the crude extract 5. The crude extract 5 was dissolved in water. Gelatin was added by a mass ratio of 3.5:10 (gelatin to the crude extract 5). The mixture was stirred for 0.5 h at a temperature of 50° C. and filtered. The filtrate was subjected to spray drying to obtain a product 5. The yield of the extract of selenium-rich *Cyclocarya paliurus* plant was 2.6%, which comprised 0.62 mg/kg of selenium and 10.8% of *Cyclocarya paliurus* polysaccharide.

Example 6

The composition of the active selenium-rich organic fertilizer was (by mass ratio): 6% of selenium-rich yeast, 48% of humic acid, 14% of cysteine, 14% of methionine, 3% of titanyl sulfate and 15% of ferrous sulfate, which were mixed to obtain the selenium-rich organic fertilizer 6. The selenium-rich organic fertilizer 6 was dissolved in water with a ratio of 1:100 to formulate an aqueous solution, which was then applied via foliar spray until leaves were wet without any visible drop of water. The fertilization was carried out once on March of Spring. Leaves were collected 15 days after spray. The content of selenium in leaves of *Cyclocarya paliurus* plant was measured to be 10.2 mg/kg.

The collected leaves of *Cyclocarya paliurus* plant as described above were purified, washed, and then smashed into 10 meshes, to obtain a first product 6. The first product 6 was weighed and added with water by a mass ratio of 1:15 (leaves to water). The extraction was carried out for 5 times under reflux for 1 h at a temperature of 100° C. After filtration, the filtrates were combined to obtain a second product 6. The second product 6 was concentrated by ultrafiltration membrane to obtain a third product 6. The volume ratio of the third product 6 to the second product 6 was 1:15. Ethanol was added into the third product 6 at a volume ratio of 3:1 (ethanol to the third product 6). After filtration, the obtained precipitate was the crude extract 6. The crude extract 6 was dissolved in water. Chitosan was added by a mass ratio of 1:10 (chitosan to the crude extract 6). The mixture was stirred for 1.5 h at a temperature of 50° C. and filtered. The filtrate was subjected to hot air drying under normal pressure to obtain a product 6. The yield of the extract of selenium-rich *Cyclocarya paliurus* plant was 7.8%, which comprised 7.4 mg/kg of selenium and 26.7% of *Cyclocarya paliurus* polysaccharide.

Example 7

The composition of the active selenium-rich organic fertilizer was (by mass ratio): 3% of selenium-rich yeast, 45% of humic acid, 20% of cysteine, 20% of methionine, 1.9% of magnesium ethylenediamine-di-o-phenyl acetate, 0.1% of sodium nitrophenolate and 10% of ferrous sulfate, which were mixed to obtain the selenium-rich organic fertilizer 7. The selenium-rich organic fertilizer 7 was dissolved in water with a ratio of 1:400 to formulate an aqueous solution, which was then applied via foliar spray until leaves were wet without any visible drop of water. The fertilization was carried out once on March of Spring. Leaves were collected 30 days after spray. The content of selenium in leaves of *Cyclocarya paliurus* plant was measured to be 5.4 mg/kg.

The collected leaves of *Cyclocarya paliurus* plant as described above were purified, washed, and then smashed into 40 meshes, to obtain a first product 7. The first product 7 was weighed and added with 0.05 mol/L Tris-HCl by a mass ratio of 1:15 (leaves to Tris-HCl). The extraction was carried out for 3 times under reflux for 2 h at a temperature of 100° C. After filtration, the filtrates were combined to obtain a second product 7. The second product 7 was concentrated under reduced pressure to obtain a third product 7. The volume ratio of the third product 7 to the second product 7 was 1:10. Ethanol was added into the third product 7 at a volume ratio of 4:1 (ethanol to the third product 7). After filtration, the obtained precipitate was the crude extract 7. The crude extract 7 was dissolved in water. Chitosan was added by a mass ratio of 5:10 (chitosan to the crude extract 7). The mixture was stirred for 0.5 h at a temperature of 50° C. and filtered. The filtrate was subjected to spray drying to obtain a product 7. The yield of the extract of selenium-rich *Cyclocarya paliurus* plant was 5.8%, which comprised 2.4 mg/kg of selenium and 25.3% of *Cyclocarya paliurus* polysaccharide.

Example 8

The composition of the active selenium-rich organic fertilizer was (by mass ratio): 5.5% of selenium-rich yeast, 40% of humic acid, 20% of cysteine, 20% of methionine, 1.5% of aspartate, 1.5% of serine, 3.5% of titanium ethylenediamine-di-o-phenyl acetate and 8% of ferrous sulfate, which were mixed to obtain the selenium-rich organic fertilizer 8. The selenium-rich organic fertilizer 8 was dissolved in water with a ratio of 1:1000 to formulate an aqueous solution, which was then applied via foliar spray until leaves were wet without any visible drop of water. The fertilization was carried out once on May of Spring. Leaves were collected 40 days after spray. The content of selenium in leaves of *Cyclocarya puliurus* plant was measured to be 3.7 mg/kg.

The collected leaves of *Cyclocarya paliurus* plant as described above were purified, washed, and then smashed into 40 meshes, to obtain a first product 8. The first product 8 was weighed and added with water by a mass ratio of 1:50 (leaves to water). The extraction was carried out for 4 times under reflux for 1 h at a temperature of 100° C. After filtration, the filtrates were combined to obtain a second product 8. The second product 8 was concentrated by ultrafiltration membrane to obtain a third product 8. The volume ratio of the third product 8 to the second product 8 was 1:20. Ethanol was added into the third product 8 at a volume ratio of 9:1 (ethanol to the third product 8). After filtration, the obtained precipitate was the crude extract 8. The crude extract 8 was dissolved in water. Gelatin was added by a mass ratio of 4:10 (gelatin to the crude extract 8). The mixture was stirred for 0.5 h at a temperature of 40° C. and filtered. The filtrate was subjected to vacuum drying to obtain a product 8. The yield of the extract of selenium-rich *Cyclocarya paliurus* plant was 5.2%, which comprised 1.8 mg/kg of selenium and 24.1% of *Cyclocarya paliurus* polysaccharide.

Example 9

The composition of the active selenium-rich organic fertilizer was (by mass ratio): 4% of selenium-rich yeast, 48% of humic acid, 22% of cysteine, 11% of methionine, 3% of zinc acetamide tetraacetate and 12% of ferrous sulfate, which were mixed to obtain the selenium-rich organic fertilizer 9. The selenium-rich organic fertilizer 9 was dissolved in water with a ratio of 1:750 to formulate an aqueous solution, which was then applied via foliar spray until leaves were wet without any visible drop of water. The fertilization was carried out once on August of Summer. Leaves were collected 35 days after spray. The content of selenium in leaves of *Cyclocarya paliurus* plant was measured to be 7.6 mg/kg.

The collected leaves of *Cyclocarya paliurus* plant as described above were purified, washed, and then smashed into 40 meshes, to obtain a first product 9. The first product 9 was weighed and added with 0.05 mol/L PBS solution by a mass ratio of 1:15 (leaves to PBS solution). The extraction was carried out for 3 times under reflux for 1.5 h at a temperature of 100° C. After filtration, the filtrates were combined to obtain a second product 9. The second product 9 was concentrated under reduced pressure to obtain a third product 9. The volume ratio of the third product 9 to the second product 9 was 1:10. Ethanol was added into the third product 9 at a volume ratio of 7:3 (ethanol to the third product 9). After filtration, the obtained precipitate was the crude extract 9. The crude extract 9 was dissolved in water. Chitosan was added by a mass ratio of 0.5:10 (chitosan to the crude extract 9). The mixture was stirred for 0.5 h at a temperature of 50° C. and filtered. The filtrate was subjected to microwave drying to obtain a product 9. The yield of the extract of selenium-rich *Cyclocarya paliurus* plant was 6.3%, which comprised 5.4 mg/kg of selenium and 26.3% of *Cyclocarya paliurus* polysaccharide.

Example 10

The composition of the active selenium-rich organic fertilizer was (by mass ratio): 10% of selenium-rich yeast, 10% of humic acid, 12% of cysteine, 24% of methionine, 14% of glutamate, 5% of titanium ethylenediamine-di-o-phenyl acetate, 2.5% of 1-methyl propylene, 2.5% of methyl jasmonate and 20% of ferrous sulfate, which were mixed to obtain the selenium-rich organic fertilizer 10. The selenium-rich organic fertilizer 10 was dissolved in water with a ratio of 1:900 to formulate an aqueous solution, which was then applied via foliar spray until leaves were wet without any visible drop of water. The fertilization was carried out once on September of Autumn. Leaves were collected 15 days after spray. The content of selenium in leaves of *Cyclocarya paliurus* plant was measured to be 5.9 mg/kg.

The collected leaves of *Cyclocarya paliurus* plant as described above were purified, washed, and then smashed into 40 meshes, to obtain a first product 10. The first product 10 was weighed and added with 20% of ethanol by a mass ratio of 1:15 (leaves to ethanol). The extraction was carried out for 3 times under reflux for 2 h at a temperature of 100° C. After filtration, the filtrates were combined to obtain a second product 10. The second product 10 was concentrated under reduced pressure to obtain a third product 10. The volume ratio of the third product 10 to the second product 10 was 1:10. Ethanol was added into the third product 10 at a volume ratio of 3:1 (ethanol to the third product 10). After filtration, the obtained precipitate was the crude extract 10. The crude extract 10 was dissolved in water. Chitosan was added by a mass ratio of 2.5:10 (chitosan to the crude extract 10). The mixture was stirred for 0.5 h at a temperature of 50° C. and filtered. The filtrate was subjected to infrared drying to obtain a product 10. The yield of the extract of selenium-rich Cyclocarya paliurus plant was 5.8%, which comprised 2.9 mg/kg of selenium and 25.8% of Cyclocarya paliurus polysaccharide.

Example 11

The composition of the active selenium-rich organic fertilizer was (by mass ratio): 6% of selenium-rich yeast, 38% of humic acid, 12% of cysteine, 24% of methionine, 5% of titanium ethylenediamine-di-o-phenyl acetate and 15% of ferrous sulfate, which were mixed to obtain the selenium-rich organic fertilizer 11. The selenium-rich organic fertilizer 11 was dissolved in water with a ratio of 1:800 to formulate an aqueous solution, which was then applied via foliar spray until leaves were wet without any visible drop of water. The fertilization was carried out once on May. Leaves were collected 25 days after spray. The content of selenium in leaves of Cyclocarya paliurus plant was measured to be 14.2 mg/kg.

The collected leaves of Cyclocarya paliurus plant as described above were purified, washed, and then smashed into 40 meshes, to obtain a first product 11. The first product 11 was weighed and added with water by a mass ratio of 1:15 (leaves to water). The extraction was carried out for 3 times under reflux for 2 h at a temperature of 100° C. After filtration, the filtrates were combined to obtain a second product 11. The second product 11 was concentrated by ultrafiltration membrane to obtain a third product 11. The volume ratio of the third product 11 to the second product 11 was 1:10. Ethanol was added into the third product 11 at a volume ratio of 3:1 (ethanol to the third product 11). After filtration, the obtained precipitate was the crude extract 11. The crude extract 11 was dissolved in water. Chitosan was added by a mass ratio of 1:10 (chitosan to the crude extract 11). The mixture was stirred for 0.5 h at a temperature of 50° C. and filtered. The filtrate was subjected to spray drying to obtain a product 11. The yield of the extract of selenium-rich Cyclocarya paliurus plant was 8.1%, which comprised 10.5 mg/kg of selenium and 27.4% of Cyclocarya paliurus polysaccharide.

Example 12

The composition of the active selenium-rich organic fertilizer was (by mass ratio): 3% of selenium-rich yeast, 42% of humic acid, 23% of cysteine, 14% of methionine, 4% of titanium ethylenediamine-di-o-phenyl acetate and 14% of diethyl sebacate, which were mixed to obtain the selenium-rich organic fertilizer 12. The selenium-rich organic fertilizer 12 was dissolved in water with a ratio of 1:500 to formulate an aqueous solution, which was then applied via foliar spray until leaves were wet without any visible drop of water. The fertilization was carried out once on April. Leaves were collected 20 days after spray. The content of selenium in leaves of Cyclocarya paliurus plant was measured to be 6.8 mg/kg.

The collected leaves of Cyclocarya paliurus plant as described above were purified, washed, and then smashed into 40 meshes, to obtain a first product 12. The first product 12 was weighed and added with water by a mass ratio of 1:15 (leaves to water). The extraction was carried out for 4 times under reflux for 1 h at a temperature of 90° C. After filtration, the filtrates were combined to obtain a second product 12. The second product 12 was concentrated under reduced pressure to obtain a third product 12. The volume ratio of the third product 12 to the second product 12 was 1:10. Ethanol was added into the third product 12 at a volume ratio of 3:2 (ethanol to the third product 12). After filtration, the obtained precipitate was the crude extract 12. The crude extract 12 was dissolved in water, and quaternary chitosan was added by a mass ratio of 1.5:10 (quaternary chitosan to the crude extract 12). The mixture was stirred for 1.5 h at a temperature of 60° C. and filtered. The filtrate was subjected to spray drying to obtain a product 12. The yield of the extract of selenium-rich Cyclocarya paliurus plant was 4.9%, which comprised 3.8 mg/kg of selenium and 22.3% of Cyclocarya paliurus polysaccharide.

Comparative Example 1

The leaves of unfertilized Cyclocarya paliurus plant were pretreated by purification and cleanout, and then smashed into 40 meshes. Water was added by a mass ratio of 1:15 (leaves to water). The extraction was carried out for 2 times under reflux for 2 h at a temperature of 100° C. After filtration, the filtrates were combined and concentrated under reduced pressure. The volume ratio of resultant concentrated solution to the filtrates was 1:10. Ethanol was added into the concentrated solution at a volume ratio of 3:1 (ethanol to the concentrated solution). After filtration, the obtained precipitate was the crude extract of Cyclocarya paliurus plant. The crude extract of Cyclocarya paliurus plant was dissolved in water. Chitosan was added by a mass ratio of 1:10 (chitosan to the crude extract). The mixture was stirred for 1 h at a temperature of 45° C. and filtered. The filtrate was subjected to spray drying to obtain an extract of Cyclocarya paliurus plant. The yield of the extract of Cyclocarya paliurus plant was 4.8%, which comprised 20.1% of Cyclocarya paliurus polysaccharide.

Example 13

The contents of metallic elements were determined in the leaves of selenium-rich Cyclocarya paliurus plant of Example 4, Example 5, Example 10 and Example 11, as well as in the leaves of unfertilized Cyclocarya paliurus plant of Comparative example 1 as control using Inductively Coupled Plasma Mass Spectrometry (ICP-MS). The results were shown as in Table 1.

TABLE 1

Test results of contents of metallic elements in leaves of selenium-rich *Cyclocarya paliurus* plant

| Experimental group | Magnesium (mg/kg) | Manganese (mg/kg) | Zinc (mg/kg) | Cuprum (mg/kg) | Chromium (mg/kg) | Nickel (mg/kg) | Vanadium (mg/kg) | Titanium (mg/kg) |
|---|---|---|---|---|---|---|---|---|
| Comparative Example 1 | 2470 | 2031.8 | 37.7 | 14.6 | 0.59 | 2.93 | 0.09 | 2.29 |
| Example 4 | 2580 | 1780.5 | 58.6 | 12.8 | 0.74 | 3.42 | 0.14 | 2.08 |
| Example 5 | 2680 | 1913.2 | 56.3 | 10.2 | 0.71 | 3.19 | 0.17 | 2.81 |
| Example 8 | 2990 | 1715.1 | 93.3 | 11.6 | 0.81 | 3.64 | 0.13 | 2.53 |
| Example 11 | 2680 | 1838.9 | 45.5 | 9.2 | 0.82 | 2.82 | 0.17 | 2.53 |

As can be seen from Table 1, no significant variation of contents of major metallic elements was found in leaves of selenium-rich *Cyclocarya paliurus* plant after application of the active selenium-rich organic fertilizer on *Cyclocarya paliurus* plant. The contents of zinc, chromium and vanadium were slightly increased, and those of manganese, cuprum and nickel were slightly decreased, and all of the contents of the above metallic elements in leaves of selenium-rich *Cyclocarya paliurus* plant were within the security scope permitted in China.

The above experiments were repeated on the products prepared in Examples 1~3, 6~9 and 12. Similar experiment results were obtained and were not further described herein.

Example 14

Long-term toxicity test in mice was carried out with the extract of selenium-rich *Cyclocarya paliurus* plant prepared in Example 11.

40 healthy Wistar rats with half female and half male were collected and randomly divided into 4 groups, namely, high dose group (6.4 g/kg), medium dose group (1.6 g/kg), low dose group (0.4 g/kg) and blank group, respectively. Each group comprised 10 rats. Extract solution of selenium-rich *Cyclocarya paliurus* plant was intragastrically administered twice daily and for 6 days weekly in each dose group (administration was paused for one day on the seventh day), for twelve consecutive weeks. Identical quantity of distilled water was administrated to the blank group. Weights were measured weekly, and activity, hair color, eating and drinking, and mentality, etc., were observed in each group of rats during the experiment. Examination of hematology and blood biochemistry indexes was performed on rats at the end of the experiment to analyze toxic reactions that might have occurred. Meanwhile, the rats were sacrificed and dissected. Main organs were taken and weighed to calculate organ coefficient. Histopathologic examination was performed on main organs.

Experiment results showed that: no obvious abnormal change was observed in activity, hair color, eating and drinking, mentality and the like in each group of rats during intragastric administration; no obvious change was observed in weight, food intake, as well as hematology and blood biochemistry indexes and organ coefficient in each dose group compared to those in the blank group; and no abnormal observation on main organs of the rats was found in the histopathologic examination.

The above experiments were repeated on the products prepared in Examples 1~10 and Example 12. Similar experiment results were obtained and thus were not further described herein.

Example 15

Comparative experiment of lowering blood glucose and blood lipid in mice was carried out with the extract of selenium-rich *Cyclocarya paliurus* prepared in Example 11 and the extract of *Cyclocarya paliurus* plant prepared in Comparative Example 1.

70 healthy male C57 mice were collected and adaptively fed with normal maintenance feed for 5 days. After fast from food overnight but not from drink, tail blood was collected to determine fasting blood glucose values, i.e. blood glucose values prior to glucose administration (0 hour). The blood glucose levels determined 0.5 hour and 2 hours after administration of 2.5 g/kg of BW glucose were taken as basal values of such batch of animals. The mice were divided into 7 groups according to the blood glucose level at 0 hour, i.e., 1 blank control group, 1 model control group, 1 positive medicament group (control medicament: Xiaoke pill), 1 medium dose group of extract of *Cyclocarya paliurus* plant (0.6 g/kg) and 3 dosage groups of extract of selenium-rich *Cyclocarya paliurus* plant (1.8 g/kg, 0.6 g/kg, 0.2 g/kg). The various dosage groups were intragastrically administrated with different dosages of test samples, respectively, the positive medicament group was administrated with 51.4 mg/100 g of Xiaoke pill, and the model control group was administrated with the same volume of solvent, for 42 consecutive days. The blank group was fed with maintenance feed, while all the other groups were fed with high fat feed. 4 weeks later, the positive medicament group, the model control group and the 4 dosage groups were respectively administrated with 40 mg/kg of streptozotocin via intraperitoneal injection based on the high fat feed, while the blank group was administrated with the same volume of citrate solution. After an interval of three days, the fasting blood glucose levels were determined, and a further injection was performed. All the groups of mice were fasted from food overnight but not from water, and the fasting blood glucose levels, i.e. the blood glucose levels prior to administration of glucose (0 hour), were determined. The dosage groups were administrated with different concentrations of test samples, the model control group was administrated with the same volume of solvent, and the blank control group was untreated. 15 minutes later, each group was orally administrated with 2.5 g/kg BW of glucose, and the blood glucose levels of each group at 0.5 hour and 2 hours after administration of glucose were determined. All the groups of mice were fasted from food overnight but not from water, and contents of total cholesterol and triglyceride in serum were determined. The determination results of blood glucose levels, oral glucose tolerance, cholesterol and triglyceride in each group of mice at 0.5 hour after intragastric administration of glucose were shown in Table 2:

TABLE 2

Determination results of blood glucose levels, oral glucose tolerance, cholesterol and triglyceride in each group of mice at 0.5 hour after intragastric administration of glucose

| | Blood glucose level at 0.5 h (mmol/L) | Oral glucose tolerance | Total cholesterol content (mmol/L) | Triglyceride content (mmol/L) |
|---|---|---|---|---|
| Blank control group | 12.9 | 18.3 | 3.62 | 1.82 |
| Model control group | 25.8 | 35.6 | 5.48 | 2.34 |
| Positive medicament group | 14.6 | 22.6 | 5.30 | 2.23 |
| Medium dosage group of Cyclocarya paliurus plant | 17.3 | 26.3 | 4.55 | 2.16 |
| High dosage group of selenium-rich Cyclocarya paliurus plant | 13.2 | 20.3 | 3.79 | 1.85 |
| Medium dosage group of selenium-rich Cyclocarya paliurus plant | 15.2 | 23.5 | 4.06 | 1.98 |
| Low dosage group of selenium-rich Cyclocarya paliurus plant | 16.7 | 27.8 | 4.23 | 2.09 |

As can be seen from Table 2, both of the extracts of selenium-rich *Cyclocarya paliurus* plant and *Cyclocarya paliurus* plant have good efficacies in lowering blood glucose, wherein the medium dosage of extract of selenium-rich *Cyclocarya paliurus* plant has an efficacy of lowering blood glucose equivalent to that of the control medicament Xiaoke pill, the low dosage of extract of selenium-rich *Cyclocarya paliurus* plant has an efficacy of lowering blood glucose equivalent to that of the medium dosage of extract of *Cyclocarya paliurus* plant, and the high dosage of extract of selenium-rich *Cyclocarya paliurus* plant has an efficacy of lowering blood glucose obviously superior to that of the control medicament Xiaoke pill. Meanwhile, the efficacies of lowering blood lipid of all of the high, medium and low dosage of extract of selenium-rich *Cyclocarya paliurus* plant are obviously superior to those of the medium dosage of extract of *Cyclocarya paliurus* plant and the control medicament Xiaoke pill.

The above experiments were repeated on the products prepared in Examples 1~10 and Example 12. Similar experiment results were obtained and thus were not further described herein.

Example 16

Comparative experiment of enhancing immunity of mice was carried out with the extract of selenium-rich *Cyclocarya paliurus* plant prepared in Example 11 and the extract of *Cyclocarya paliurus* plant prepared in Comparative Example 1.

The activities of superoxide dismutase (SOD) and glutathione peroxidase (GSH-Px) in serum of each group of mice in Example 15 were determined. The spleens of mice were taken to perform an MTT transformation experiment on mouse spleen immune cells to determine the stimulation indexes (SI). The results were shown in Table 3.

TABLE 3

Determination results of immunity indexes in each group of mice.

| | Serum SOD value (U/mL) | Serum GSH-Px value (U/mL) | MTT experiment SI value |
|---|---|---|---|
| Blank control group | 37.53 | 78.16 | 1.156 |
| Model control group | 40.28 | 88.24 | 1.135 |
| Positive medicament group | 43.92 | 96.82 | 1.147 |
| Medium dosage group of Cyclocarya paliurus plant | 47.31 | 221.87 | 1.169 |
| High dosage group of selenium-rich Cyclocarya paliurus plant | 62.06 | 515.65 | 1.296 |
| Medium dosage group of selenium-rich Cyclocarya paliurus plant | 56.75 | 458.29 | 1.237 |
| Low dosage group of selenium-rich Cyclocarya paliurus plant | 48.64 | 336.13 | 1.183 |

As can be seen from Table 3 that, it is illustrated by the activity of SOD and GSH-Px in mouse serum, as well as the SI value from the MTT transformation experiment on mouse spleen immune cells that, the extract of selenium-rich *Cyclocarya paliurus* plant can significantly enhance the immune function in mice, and the immunity enhancing efficacies in mice of all the low, medium and high dosage of extract of selenium-rich *Cyclocarya paliurus* plant are obviously superior to those of the medium dosage of extract of *Cyclocarya paliurus* plant and the control medicament Xiaoke pill. Moreover, with the increasing dosage of the extract of selenium-rich *Cyclocarya paliurus* plant, the immunity enhancing efficacy is improved notably as well.

The above experiments were repeated on the products prepared in Examples 1~10 and Example 12. Similar experiment results were obtained and thus were not further described herein.

In view of the above, a method for cultivation of a selenium-rich *Cyclocarya paliurus* plant as well as extraction and application of active ingredients thereof provided in examples of the present invention overcome the disadvantages of high residue, poor absorption, and less environmental friendliness of fertilizers used in cultivation of a selenium-rich plant in the prior art, and meanwhile overcome the disadvantages of low absorption rate and high adverse reaction rate in current extraction method and application of active ingredients in a selenium-rich plant.

The above described contents are merely preferred embodiments of the present invention. It should be noted that, for an ordinary skilled in the art, some improvements and modifications without departing from the principles of the present invention can be made, which should also construed to be within the protection scope the present invention.

The invention claimed is:

1. A method of cultivating a selenium-containing *Cyclocarya paliurus* plant comprising
    applying a selenium-containing fertilizer consisting of 6% of selenium-rich yeast, 38% of humic acid, 12% of cysteine, 24% of methionine, 5% of titanium ethylene-diamine-di-o-phenyl acetate and 15% of ferrous sulfate by mass ratio via foliar spray to a *Cyclocarya paliurus* plant.

2. The method according to claim 1, further comprising dissolving the selenium-containing fertilizer in water by a mass ratio of 1:800 to formulate an aqueous solution prior to performing foliar spray.

* * * * *

UNITED STATES PATENT AND TRADEMARK OFFICE
CERTIFICATE OF CORRECTION

PATENT NO. : 10,420,811 B2  
APPLICATION NO. : 15/367372  
DATED : September 24, 2019  
INVENTOR(S) : Weihong Chen et al.

Page 1 of 1

It is certified that error appears in the above-identified patent and that said Letters Patent is hereby corrected as shown below:

On the Title Page

Item (71) Applicant, delete the entirety of the item and replace with --INFINITUS (CHINA) COMPANY LTD., Jiang Men City (CN)-- therefor.

Item (72) Inventors, delete the entirety of the item and replace with --Weihong CHEN, Jiang Men City (CN); Fangli MA, Jiang Men City (CN); Wei LIU, Jiang Men City (CN); Meng LV, Jiang Men City (CN); Chung Wah MA, Jiang Men City (CN)-- therefor.

Item (73) Assignee, delete the entirety of the item and replace with --INFINITUS (CHINA) COMPANY LTD., Jiang Men City, (CN)-- therefor.

Signed and Sealed this  
Twenty-ninth Day of October, 2019

Andrei Iancu  
*Director of the United States Patent and Trademark Office*